United States Patent [19]

Nishimura

[11] Patent Number: 4,558,273

[45] Date of Patent: Dec. 10, 1985

[54] APPARATUS FOR THE INSPECTION OF ELECTRODEPOSITED ELECTRICALLY INSULATING COATINGS

[75] Inventor: Tsugio Nishimura, Itami, Japan

[73] Assignee: Mitsubishi Denki Kabushiki Kaisha, Tokyo, Japan

[21] Appl. No.: 500,231

[22] Filed: Jun. 1, 1983

[51] Int. Cl.[4] ............................................ G01R 31/12
[52] U.S. Cl. ....................................................... 324/54
[58] Field of Search ................. 118/665, 712; 427/10; 204/413; 324/51, 62, 52, 54

[56] References Cited

U.S. PATENT DOCUMENTS 2,622,129 12/1952 Killian ..................................... 324/54
3,414,808 12/1968 Thomas ................................... 324/54

Primary Examiner—Stanley T. Krawczewicz
Assistant Examiner—Jose M. Solis
Attorney, Agent, or Firm—Wenderoth, Lind & Ponack

[57] ABSTRACT

The apparatus according to the present invention for inspecting the quality of electrodeposited electrically insulating coatings on electrically conducting parts comprises wetting means for producing a high pressure, low flow volume spray of an electrically conducting liquid and means for producing a low pressure, high flow volume column of the same conducting liquid. It further comprises a conveyor which carries the part to be inspected through the spray produced by the wetting means and through the liquid column, as well as means for applying a voltage between the part and the liquid column and for measuring the resulting current when the part to be inspected passes through the liquid column. The high pressure spray produced by the wetting means thoroughly wets the part to be inspected and prevents air bubbles from adhering to the part, air bubbles being an impediment to correct current measurement. The measured current is an indication of the quality of the insulating coating.

5 Claims, 5 Drawing Figures

APPARATUS FOR THE INSPECTION OF ELECTRODEPOSITED ELECTRICALLY INSULATING COATINGS

BACKGROUND OF THE INVENTION

This invention relates to the electrodeposition of electrically insulating coatings on electrically conducting parts, and in particular, it relates to an apparatus for the inspection of the quality of such coatings by means of electrical measurements.

One type of presently used apparatus for inspecting electrodeposited electrically insulating coatings is shown in FIG. 1. In the figure, reference numeral 1 is an electrically conducting part which has been coated by electrodeposition with an electrically insulating coating. Reference numeral 2 designates is a conveyor for transporting the part 1 during the inspection process. The part 1 is suspended from the conveyor 2 by a suspending device 3 connected to the conveyor 2. Reference numeral 4 designates a tank filled with an electrically conducting liquid 5. Reference numeral 6 designates an elevating device for raising and lowering the tank 4 containing the electrically conducting liquid 5. The elevating device 6 comprises a column 6a mounted on a base 6b, a chain 6c connected to the tank 4, and a motor (not shown) for driving the chain 6c, thereby raising or lowering the tank 4.

The operation of this apparatus is as follows. The conducting part 1 covered with an insulating coating is positioned directly above the tank 4 by the conveyor 2. The tank 4 is then raised automatically by the elevating device 6 until the part 1 is almost completely immersed in the conducting liquid 5. A voltage is then applied between the conducting part 1 and the side of the tank 4 for a predetermined length of time, and the resulting current is measured. The level of the current and the rise time of the current indicate the quality of the insulating coating; if the coating completely covers the conducting part 1, no current will be able to flow between the part 1 and the side of the tank 4. On the other hand, if the coating is very irregular or contains pin holes, the conducting liquid 5 will quickly penetrate to the conducting part 1, and a large current will result. After a predetermined length of time, the tank 4 is lowered and the part 1 is carried off by the conveyor 2 in the direction shown by the arrow.

FIG. 2 shows another commonly used inspection apparatus. It is similar in construction to the apparatus of FIG. 1 and operates on basically the same principles. It differs only in that the tank 4 does not move up and down and in that it is not necessary to stop the forward motion of the part 1 in order to inspect the insulating coating. The conveyor 2 is shaped so that the part 1 is dipped into the conducting liquid 5 during its forward motion. While it is passing through the liquid 5, a voltage is applied between the part 1 and the side of the tank 4, and the current flowing between the two is measured.

Unfortunately, inspection carried out using the apparatuses shown in FIGS. 1 and 2 is often inaccurate. These apparatuses include no means for preventing air bubbles from adhering to the part 1 being inspected. Whereas the conducting liquid 5 should penetrate to the conducting part 1 in locations where the insulating coating is inadequate, if air bubbles adhere to these locations, the liquid 5 will be prevented from penetrating. Accordingly, the current flowing between the part 1 and the side of the tank 4 will be misleadingly low and will not give a correct indication of the quality of the insulating coating.

Furthermore, both apparatuses have the drawback that they entail both horizontal and vertical movement, which makes structure of the apparatuses unnecessarily complicated and increases their cost.

Another method of inspecting insulating coatings is to apply a thin, electrically conducting foil to the part 1 to be inspected, apply a voltage between the part 1 and the foil, and measure the dielectric strength of the insulating coating. However, the application of the foil requires considerable effort, and this method is not suitable for mass production.

SUMMARY OF THE INVENTION

It is an object of the present invention to provide an apparatus for inspecting electrodeposited electrically insulating coatings which is more accurate than presently existing apparatuses.

It is another object of the present invention to provide an apparatus for inspecting electrodeposited electrically insulating coatings which has a simple structure.

The apparatus according to the present invention causes an electrically conducting part which has been covered with an insulating coating to be passed through a high flow volume, low pressure column of an electrically conducting liquid. While it is being passed through this column, a voltage is applied between the conducting part and the liquid column, and the resulting current is measured as an indication of the quality of the coating. Before being passed through the liquid column, the conducting part passes through a low flow volume, high pressure liquid spray which thoroughly wets the part so that no air bubbles will adhere to it when it passes through the liquid column. Because no air bubbles adhere to the part, the current flowing between the liquid column and the part to be inspected is an accurate indication of the quality of the insulating coating.

The apparatus for inspecting electrodeposited electrically insulating coatings according to the present invention comprises a tank having an input opening and an output opening, wetting means for thoroughly wetting the electrically conducting part to be inspected with an electrically conducting liquid, means for producing a low pressure column of the electrically conducting liquid, conveyor means extending through the tank for conveying a part to be inspected past the wetting means and through the low pressure liquid column in succession, and current measuring means for applying a voltage between the liquid column and the part to be inspected and for measuring the resulting current.

DESCRIPTION OF THE PREFERRED EMBODIMENT

Figure 1:
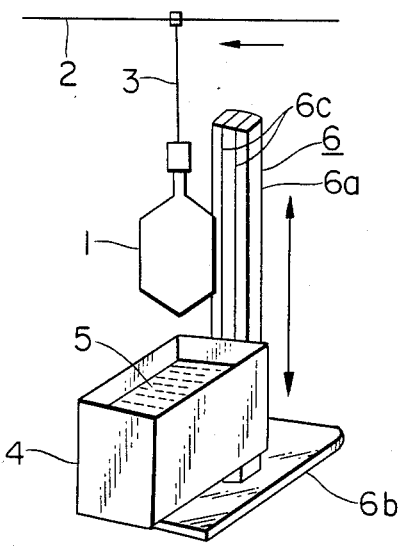
FIG. 1 is a perspective view of one type of presently used apparatus for inspecting insulating coatings.

One embodiment of an apparatus for inspecting electrically insulating coatings according to the present invention will now be described in detail while making reference to FIGS. 3 and 4, which show a perspective view and a schematic of this embodiment. In the figures, reference numerals identical to those used in FIGS. 1 and 2 refer to identical or corresponding parts.

The tank 4 has high sides in which have been formed an input opening and an output opening. The conveyor 2 extends through these openings parallel to the axis of the tank 4. Reference numeral 7 designates high pressure nozzles secured to both sides of the tank 4 along its entire length. Reference numeral 8 designates low pressure nozzles pointing downwards and secured to both sides of the tank 4 at a single location on each side. Reference numeral 9 designates high pressure volume flow regulators connected to each high pressure nozzle 7, and reference numeral 10 designates low pressure volume flow regulators connected to each low pressure nozzle 8. Reference numeral 11 designates a circulating pump connected to the bottom of the tank 4 and to the volume flow regulators 9 and 10. Reference numeral 12 designates stop valves disposed between the pump 11 and the volume flow regulators 9 and 10. The high pressure nozzles 7, the high pressure volume flow regulators 9, the pump 11, and the stop valves 12 together consitute wetting means for thoroughly wetting with the conducting liquid 5 an electrically conducting part 1 to be inspected, and the low pressure nozzles 8, the low pressure volume flow regulators 10, the pump 11, and the remaining stop valves 12 together constitute means for producing a low pressure column of the conducting liquid 5.

Reference numeral 13 a DC power source having one terminal connected to the conveyor 2 via a switch 14 and having the other terminal connected via an amplifier 15 to one of the low pressure nozzles 8 (if the nozzle 8 is made of a conducting material) or else to one of the liquid columns 18 emerging therefrom. The conducting part 1 is electrically connected to the conveyor 2 by the suspending device 3, so that when the switch 14 is closed, the conducting part 1 is also in electrical contact with the DC source 13.

The switch 14 is operated by a position sensor 16 mounted directly above one of the low pressure nozzles 8. Reference character 3a designates a horizontal projection formed on the suspending device 3 designed so as to physically contact the sensor 16 when passing by it, causing the sensor 16 to close the switch 14.

The DC power source 13, the switch 14, and the amplifier 15 together constitute current measuring means for applying a voltage between the conducting part 1 and the liquid column 18 and for measuring the resulting current.

Figure 3:
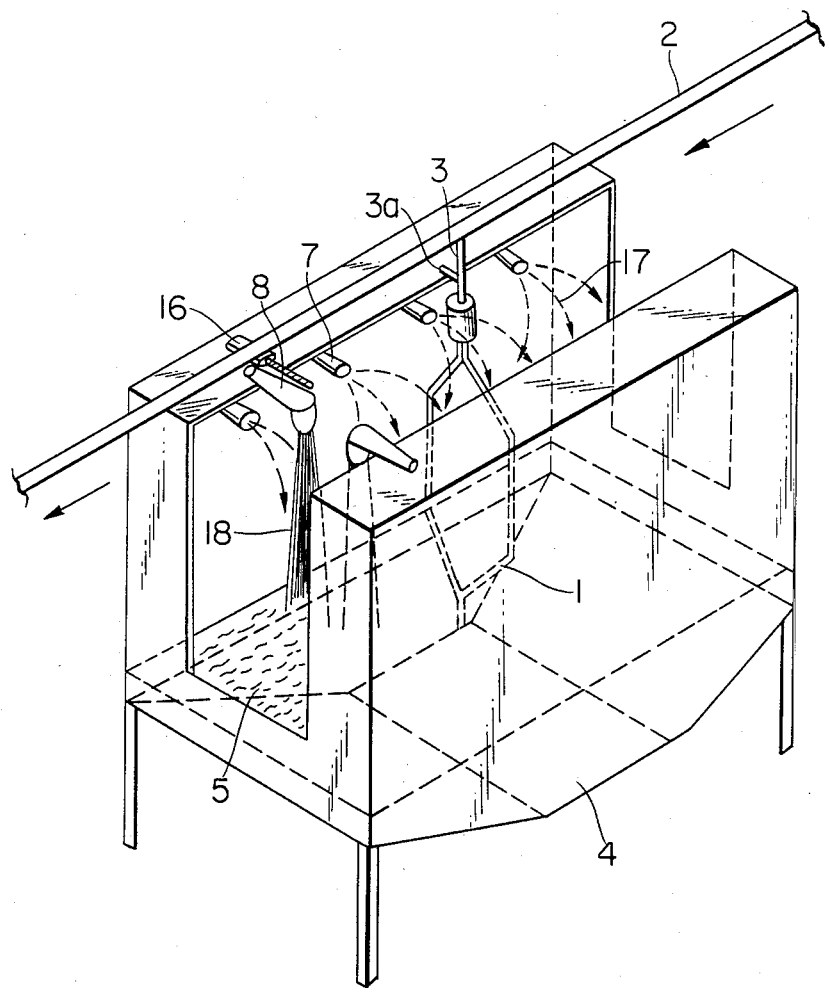
FIG. 3 is a partial perspective view of an embodiment of an apparatus for inspecting insulating coatings according to the present invention.
Figure 4:
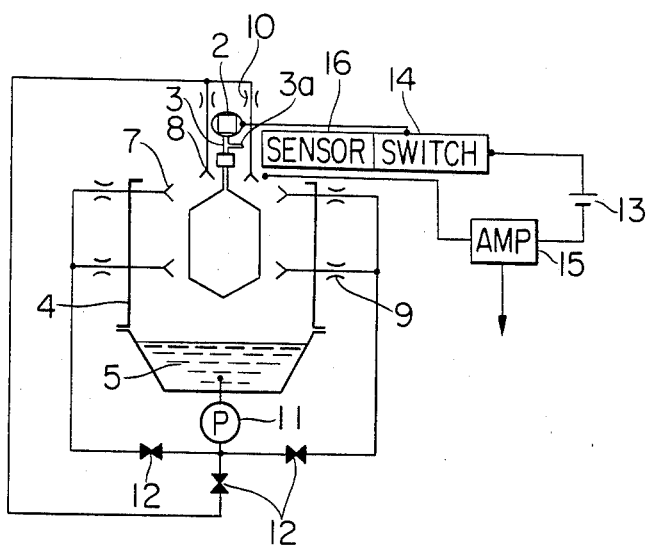
FIG. 4 is a schematic diagram of the embodiment illustrated in FIG. 3.

The operation of the embodiment shown in FIGS. 3 and 4 is as follows. While a conducting part 1 to be inspected is being conveyed by the conveyor 2 in the direction shown by the arrow, the pump 11 continuously draws conducting liquid 5 from the tank 4 and pumps it through the stop valves 12 and the high pressure volume flow regulators 9. The liquid 5 emerges from the low pressure nozzles 7 as a high pressure, low flow volume spray 17. The conducting part 1 is carried through this spray 17 and is thoroughly wet by the conducting liquid 5.

At the same time, the pump 11 continuously pumps conducting liquid 5 through a stop valve 12 and the low pressure volume flow regulators 10, and conducting liquid 5 emerges from the low pressure nozzles 8 as low pressure, high flow volume liquid columns 18. When the part enters these liquid columns 18, the horizontal projection 3a on the suspending device 3 contacts the position sensor 16, causing the sensor 16 to close the switch 14, thus electrically connecting the conducting part 1 with the positive terminal of the DC power supply 13 via the conveyor 2. Any current flowing between the conducting part 1 and the liquid column 18 also flows through the amplifier 15, by which it is amplified. The output of the amplifier 15 is recorded as a function of time and used to determine the quality of the insulating coating covering the conducting part 1.

Figure 5:
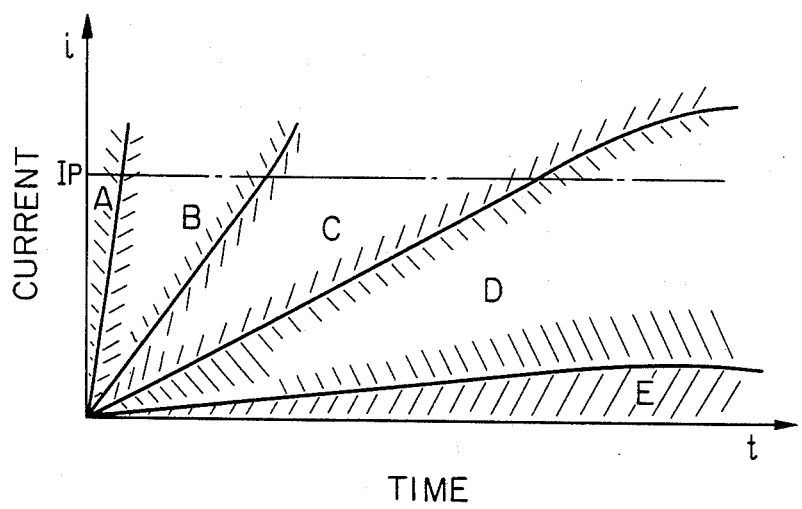
FIG. 5 is a graph of the relationship between time (t) and current (i) flowing between the part being inspected and the conducting liquid during inspection of an insulating coating using the embodiment pictured in FIGS. 3 and 4.

FIG. 5 shows the results of current measurements made using the embodiment of FIGS. 3 and 4. In the figure, the abscissa is time and the ordinate is current. When the insulating coating contains a pin hole with a diameter of 1 mm or greater, the conducting liquid 5 can flow directly to the conducting part 1, resulting in a large current in a very short time. The current vs time curve for such a coating would fall into Region A of FIG. 5.

If the insulating coating contains pin holes on the order of a few hundred microns in diameter, conducting liquid 5 penetrates through the coating to the conducting part 1 by capillary action, taking considerably longer time than for a 1 mm pin hole. In this case, the curve of current vs time would fall into Region B of the figure.

When the arrangement of the particles of the insulating material which composes the coating is disorderly and the particles do not form regular laminations, the conducting liquid 5 is able to penetrate to the conducting part 1, but the current levels and the rise times are much lower than when the coating has pin holes extending all the way through the coating (Regions A and B). The curves of current vs time for such a coating would fall into Regions C or D, depending on how disorderly the arrangement of the particles.

Region E is for a coating comprising particles having a high aspect ratio (average length of particles × average width/average thickness) such as mica, which has an aspect ratio of around 1000. Even though spaces exist between individual mica particles, the particles form smooth, regular laminations which impede the penetration of the conducting liquid, and accordingly very little current flows.

As can be seen from FIG. 5, there is a very clear difference not only in current levels but also in the rise times of the currents depending on the state of the insulating coating. By measuring the time for the current to reach an arbitrary value $I_p$ or alternatively by measuring the current level at an arbitrary time after a voltage is applied, the quality of the coating can be determined with considerable accuracy.

Because the conducting part 1 is thoroughly wetted by the high pressure spray 17 before being introduced into the low pressure liquid column 18, no air bubbles adhere to the part 1, and there is no impediment preventing the conducting liquid 5 from penetrating through any holes in the insulating coating. The current measured when the part 1 is beneath the liquid column 18 will thus be an accurate indication of the coating quality, making the inspection apparatus according to the present invention superior to apparatuses of the types shown in FIGS. 1 and 2.

Figure 2:
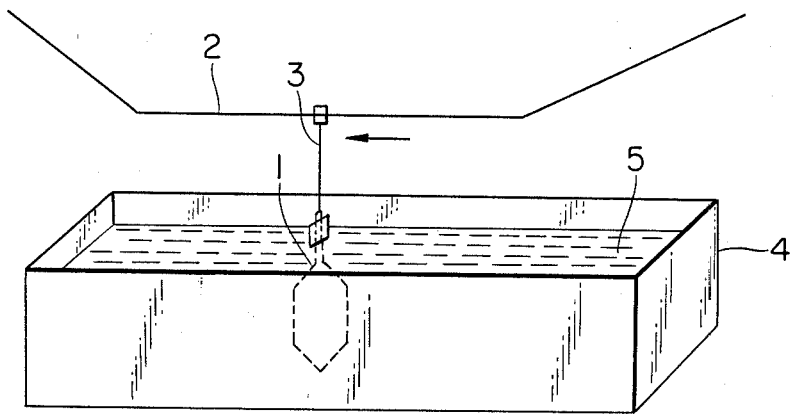
FIG. 2 is a perspective view of another type of presently used apparatus for inspecting insulating coatings.

The present invention has the further advantage that it entails motion only of the conducting part 1 and motion only in a horizontal plane, permitting it to be of simpler structure than the apparatuses of FIGS. 1 and 2 which entail vertical as well as horizontal movement.

Although the present embodiment employs a single pump 11 for supplying conducting liquid 5 to both the low pressure nozzles 7 and the high pressure nozzles 8, it may be desirable to use two separate pumps (a first pump which is a high presssure pump for the high pressure nozzles, and a second pump which is a low pressure pump for the low pressure nozzles) so that each pump can operate at maximum pump efficiency.

The wetting means employed in the present embodiment produces a high pressure spray of the conducting liquid 1, but wetting means which produce a vapor formed from the conducting liquid 1 may be employed with the same effect. In this case, the wetting means would comprise a boiler for vaporizing the conducting liquid 5 instead of a circulating pump.

What is claimed is:

1. An apparatus for inspecting electrodeposited electrically insulating coatings comprising;
    a tank having an input opening and an output opening;
    wetting means for thoroughly wetting with an electrically conducting liquid an electrically conducting part which has been covered with an electrically insulating coating;
    means for producing a low pressure, high flow volume liquid column of said conducting liquid;
    conveyor means, extending through said tank through said input and output openings, for conveying said electrically conducting part past said wetting means and through said low pressure liquid column in succession; and
    current measuring means for applying a voltage between said electrically conducting part and said liquid column when said part passes through said liquid column and for measuring the resulting current.

2. An apparatus as claimed in claim 1, wherein said wetting means comprise a first circulating pump connected to the bottom of said tank, a high pressure volume flow regulator connected to the output end of said first pump, and a low pressure nozzle mounted on the side of said tank and connected to said high pressure volume flow regulator.

3. An apparatus as claimed in claim 2, wherein said means for producing a liquid column comprise a second circulating pump connected to the bottom of said tank, a low pressure volume flow regulator connected to the output end of said second pump, and a low pressure nozzle mounted on the side of said tank and connected to said low pressure regulator.

4. An apparatus as claimed in claim 1, wherein said wetting means and said means for producing a liquid column comprise a circulating pump having an output end, connected to the bottom of said tank, said wetting means further comprising a high pressure volume flow regulator connected to said output end of said pump, and a low pressure nozzle mounted on the side of said tank and connected to said high pressure volume flow regulator, said means for producing a liquid column further comprising a low pressure volume flow regulator connected to said output end of said pump, and a low pressure nozzle mounted on the side of said tank and connected to said low pressure volume flow regulator.

5. An apparatus as claimed in claim 4, further comprising position sensing means for determining when a conducting part to be inspected has entered said liquid column and for activating said current measuring means at that time.

* * * * *